United States Patent [19]

Beck et al.

[11] Patent Number: 5,204,351
[45] Date of Patent: Apr. 20, 1993

[54] 6-FLUORO-3,5-DIHYDROXY CARBOXYLIC ACIDS AND DERIVATIVES THEREOF

[75] Inventors: Gerhard Beck, Frankfurt am Main; Wilhelm Bartmann, Bad Soden am Taunus; Günther Wess, Erlensee; Ernold Granzer, Kelkheim, all of Fed. Rep. of Germany

[73] Assignee: Hoechst Aktiengesellschaft, Frankfurt am Main, Fed. Rep. of Germany

[21] Appl. No.: 389,809

[22] Filed: Aug. 4, 1989

[30] Foreign Application Priority Data

Aug. 6, 1988 [DE] Fed. Rep. of Germany ....... 3826814

[51] Int. Cl.$^5$ ................ A61K 31/495; C07D 239/26; C07D 403/06
[52] U.S. Cl. .................................... 514/256; 544/333; 544/335
[58] Field of Search ................ 544/333, 335; 514/256

[56] References Cited

U.S. PATENT DOCUMENTS

| | | | |
|---|---|---|---|
| 4,681,893 | 7/1987 | Roth | 514/422 |
| 4,868,185 | 9/1989 | Chucholowski et al. | 514/256 |
| 4,925,852 | 5/1990 | Kesseler et al. | 514/333 |

OTHER PUBLICATIONS

M. R. Boots et al., Pharm. Sci. vol. 69 (1980) pp. 506–509.

F. M. Singer et al., Proc. Soc. Exper. Biol. Med., vol. 102 (1959), pp. 370–373.

H. Ferres et al., Tetrahedron Letters vol. 24, (1983), pp. 3769–3772.

G. E. Stokker et al., J. Med. Chem., vol. 29, pp. 170–181 (1986).

*Primary Examiner*—Nicholas S. Rizzo
*Assistant Examiner*—Y. N. Gupta
*Attorney, Agent, or Firm*—Finnegan, Henderson, Farabow, Garrett & Dunner

[57] ABSTRACT

6-Fluoro-3,5-dihydroxy carboxylic acid derivatives of the formula I and the corresponding lactones of the formula II in which $R^1$ and $R^2$ have the specified meanings, a process for the preparation of these compounds, the use thereof as medicinal agents and pharmaceutical products are described. In addition, new intermediates for the preparation of the compounds of the formula I or formula II are described.

3 Claims, No Drawings

6-FLUORO-3,5-DIHYDROXY CARBOXYLIC ACIDS AND DERIVATIVES THEREOF

DESCRIPTION

The enzyme 3-hydroxy-3-methylglutaryl-coenzyme A reductase (HMG-CoA reductase) catalyzes the formation of mevalonic acid from 3-hydroxy-3-methylglutaryl-coenzyme A (HMG-CoA). This reaction plays a central part in the biosynthesis of cholesterol. Derivatives of 3-hydroxy-3-methylglutaric acid (HMG) and of mevalonic acid have been described as inhibitors of cholesterol biosynthesis (M. R. Boots et al., J. Pharm. Sci. 69, 306 (1980), F. M. Singer et al., Proc. Soc. Exper. Biol. Med. 102, 270 (1959), H. Feres, Tetrahedron Lett. 24, 3769 (1983)). 3-Hydroxy-3-methylglutaric acid itself shows a significant cholesterol-lowering action in rats and in tests on humans (Z. Beg, Experientia 23, 380 (1967), ibid 24, 15 (1968), P. J. Lupien et al., Lancet 1978, 2, 283).

It has now been found that the fluoro dihydroxy carboxylic acids of the general formula I, as well as the corresponding lactones of the formula II, are inhibitors of HMG-CoA reductase.

The invention therefore relates to 6-fluoro-3,5-dihydroxy carboxylic acids and derivatives thereof of the general formula I

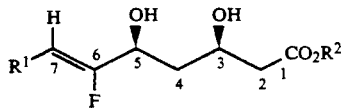

and the corresponding lactones of the formula II

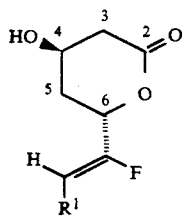

In the general formulae I and II,
$R^1$ denotes
A) the group of substituted 6-membered ring aromatics and heteroaromatics a, b, c

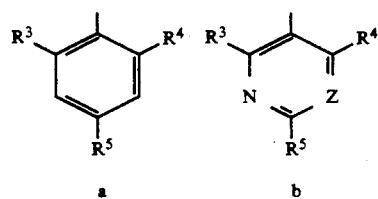

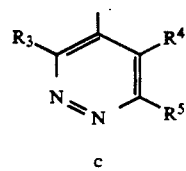

in which

Z denotes a radical of the formula —CH or a nitrogen atom, $R^3$, $R^4$ and $R^5$ independently of one another denote hydrogen, a straight-chain or branched alkyl or alkenyl radical, each of which has up to 6 carbon atoms and which can optionally be substituted on the terminal carbon by a cycloalkyl or cycloalkenyl radical, each of which has 3–6 carbon atoms, or denote a cyclic hydrocarbon radical which is saturated or up to doubly unsaturated and has 3–7 carbon atoms, or an aromatic radical selected from the group comprising phenyl, furyl, thienyl and pyridinyl, which can optionally carry in the nucleus 1–3 identical or different substituents from the following group: halogen, trifluoromethyl, alkyl or alkenyl, each of which has up to 6 carbon atoms, hydroxyl, alkoxy having 1–6 carbon atoms, carboxyl or carbalkoxy having 1–6 carbon atoms in the alkoxy moiety, B) the group of substituted 5-membered ring heteroaromatics

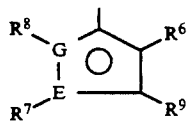

in which G—E denotes the following atomic sequences
a) N—C (1H-pyrrol-2-yl)
b) S—C (2-thienyl)
c) C—N (1H-pyrrol-3-yl)
d) C—O (3-furyl)
e) C—S (3-thienyl)
and $R^6$ denotes H, straight-chain $C_1$–$C_4$-alkyl, $C_3$–$C_6$-branched alkyl, trifluoromethyl, halogen or phenyl which is optionally substituted 1–2 times by fluorine, chlorine or methyl, $R^7$ denotes H, straight-chain $C_1$–$C_4$-alkyl, branched $C_3$–$C_6$-alkyl, trifluoromethyl, halogen or phenyl, $R^8$ denotes H, cycloalkyl having 5–8 ring carbon atoms, branched $C_3$–$C_6$-alkyl, or phenyl, which can in turn be substituted 1–2 times by straight-chain $C_1$–$C_3$-alkyl, halogen or trifluoromethyl, and $R^9$ denotes H, straight-chain $C_1$–$C_3$-alkyl, branched $C_3$–$C_6$-alkyl, cycloalkyl having 5–8 ring carbon atoms, trifluoromethyl or phenyl which can in turn be substituted 1–2 times by straight-chain $C_1$–$C_3$-alkyl, halogen or trifluoromethyl, and $R^7$ and $R^9$ together also denote a conjugated unsaturated radical having 4 carbon atoms, so that $R^7$ and $R^9$ form a fused-on aromatic moiety, and in which the substituents $R^7$ and $R^8$ are absent in those heteroaromatics which have oxygen and sulfur at the relevant positions, or C) the group of substituted olefins

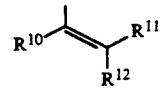

in which $R^{10}$, $R^{11}$ and $R^{12}$ independently of one another denote a straight-chain or branched alkyl or alkenyl radical, each of which has up to 6 carbon atoms and can optionally be substituted on the terminal carbon by a cycloalkyl or cycloalkenyl radical, each of which has 3-6 carbon atoms, or denote a cyclic hydrocarbon radical which is saturated or up to doubly unsaturated and has 3-7 carbon atoms or an aromatic radical selected from the group comprising phenyl, furyl, thienyl or pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl or carbalkoxy having 1-6 carbon atoms in the alkoxy moiety, and $R^2$ denotes hydrogen, a straight-chain or branched alkyl or alkenyl radical, each of which has up to 8 carbon atoms, a benzyl radical whose nucleus can be substituted 1-2 times by halogen or an alkyl radical having 1-4 carbon atoms, or denotes alkali metal or an ammonium ion $NR^{13}R^{14}R^{15}R^{16}$, where $R^{13}$, $R^{14}$, $R^{15}$ and $R^{16}$ are identical or different and denote hydrogen, alkyl having 1-4 carbon atoms or hydroxyalkyl having 1-4 carbon atoms.

The invention relates to the pure enantiomers having the absolute configuration 3R, 5S specified in the general formula I or the absolute configuration 4R, 6S depicted in formula II.

If $R^1$ denotes the group specified under A, the following applies:

Preferred among the substituents $R^3$ and $R^4$ are a straight-chain or branched alkyl radical having 1-4 carbon atoms, a cycloalkyl radical having 5-6 carbon atoms, a cycloalkylmethyl or cycloalkenylmethyl radical having a ring size of 5-6 carbon atoms, a phenyl radical which can optionally carry 1-3 identical or different substituents from the following group: halogen, trifluoromethyl, alkyl having 1-4 carbon atoms, hydroxyl, alkoxy having 1-4 carbon atoms or carbalkoxy having 1-4 carbon atoms in the alkoxy moiety.

Preferred among the meanings for $R^5$ are hydrogen, a straight-chain or branched alkyl or alkenyl radical, each of which has up to 6 carbon atoms, a cycloalkyl or cycloalkenyl radical, each of which has 5-6 carbon atoms, a phenyl or pyridinyl radical, it being possible for the aromatic radicals optionally to carry 1-3 identical or different substituents from the following groups: halogen, alkyl having 1-4 carbon atoms, hydroxyl, alkoxy having 1-4 carbon atoms or carbalkoxy having 1-4 carbon atoms in the alkoxy moiety.

Particularly preferred among the substituents $R^3$ are: methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl and 4-trifluoromethylphenyl.

Particularly preferred among the substituents $R^4$ are: methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl and 4-trifluoromethylphenyl.

Particularly preferred among the substituents $R^5$ are: hydrogen, methyl, isopropyl, tert.-butyl, cyclohexyl, phenyl, 4-fluorophenyl, 2,5-dimethylphenyl, 3,5-dimethylphenyl and 4-trifluoromethylphenyl.

If $R^1$ denotes the group specified under B, the following applies:

Preferred among the substituents $R^6$ are: H, methyl, ethyl, propyl, isopropyl, t-butyl and trifluoromethyl.

Preferred among the substituents $R^7$ are: straight-chain $C_1$-$C_4$-alkyl, branched $C_3$-$C_6$-alkyl, trifluoromethyl and phenyl.

Preferred among the substituents $R^8$ are: cycloalkyl having 5 or 6 ring carbon atoms, or phenyl which can in turn be substituted 1 or 2 times by methyl, ethyl, chlorine, bromine, fluorine or trifluoromethyl.

Preferred among the substituents $R^9$ are straight-chain $C_1$-$C_3$-alkyl, branched $C_3$-$C_6$-alkyl, trifluoromethyl, or phenyl which can in turn be substituted 1 or 2 times by methyl, ethyl, propyl, trifluoromethyl, chlorine or fluorine.

Particularly preferred among the substituents $R^6$ are those mentioned hereinafter: methyl, isopropyl, tertiary-butyl and trifluoromethyl.

Particularly preferred among the substituents $R^7$ are: methyl, isopropyl, tertiary-butyl, trifluoromethyl and phenyl.

If $R^1$ denotes the group specified under C, the following applies:

Preferred among the substituents $R^{10}$ and $R^{11}$ are: a straight-chain or branched alkyl radical having 1-4 carbon atoms, a cycloalkyl radical having 5-6 carbon atoms, a cycloalkylmethyl or cycloalkenylmethyl radical having a ring size of 5-6 carbon atoms, a phenyl radical which can optionally carry 1-3 identical or different substituents from the following group: halogen, trifluoromethyl, alkyl having 1-4 carbon atoms, hydroxyl, alkoxy having 1-4 carbon atoms or carbalkoxy having 1-4 carbon atoms in the alkoxy moiety.

Preferred among the meanings for $R^{12}$ are a straight-chain or branched alkyl or alkenyl radical each having up to 6 carbon atoms, a phenyl or pyridinyl radical, it being possible for the aromatic radicals optionally to carry 1-3 identical or different substituents from the following groups: halogen, alkyl having 1-4 carbon atoms, hydroxyl, alkoxy having 1-4 carbon atoms or carbalkoxy having 1-4 carbon atoms in the alkoxy moiety.

Particularly preferred among the substituents $R^{10}$ are methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl or 4-trifluoromethylphenyl.

Particularly preferred among the substituents $R^{11}$ are: phenyl, 4-chlorophenyl, 4-fluorophenyl, 4-methoxyphenyl, 4-fluoro-3-methylphenyl, 3,5-dimethylphenyl, cyclohexylmethyl and 4-trifluoromethylphenyl.

Particularly preferred among the substituents $R^{12}$ are phenyl, 4-fluorophenyl, 2,5-dimethylphenyl, 4-fluoro-3-methylphenyl, 3,5-dimethylphenyl and 4-trifluoromethylphenyl.

The invention furthermore relates to a process for the preparation of the compounds of the general formulae I and II, which comprises a) converting appropriately substituted aldehydes of the formula III

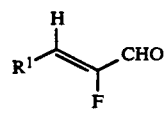

III in which $R^1$ has the specified meaning, into the corresponding hydroxy esters of the general formula IV

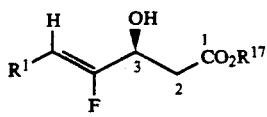

in which $R^1$ has the specified meaning, and $R^{17}$ represents a suitable optically active acid protecting group which determines the stereochemistry at C-3, or an alkyl radical having 1-8 carbon atoms b) converting the optically active compounds of the formula IV with achiral acetic ester enolates either directly or after previous conversion into the corresponding alkyl esters, preferably methyl esters, into the optically active compounds of the formula V

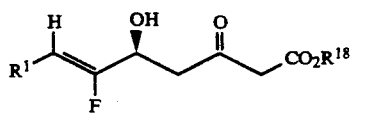

in which $R^1$ has the specified meaning, and $R^{18}$ is alkyl having 1-8 carbon atoms, c) converting the hydroxy keto esters of the formula V into the corresponding 6-fluoro-3,5-dihydroxy compounds of the formula I

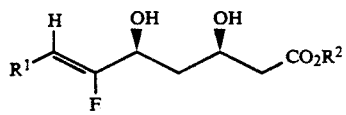

in which $R^1$ has the meaning specified for formula I, and $R^2$ is alkyl having 1-8 carbon atoms, and, where appropriate, hydrolyzing a resulting compound to a compound of the formula I in which $R^2$ represents a metal cation, where appropriate liberating therefrom the free acid ($R^2$=hydrogen), and where appropriate converting the free acid into compounds of the formula I with $R^2$=alkyl or alkenyl, each having up to 8 carbon atoms, ammonium ion, benzyl or appropriately substituted benzyl, d) and converting a resulting compound of the formula I where appropriate into a lactone of the formula II

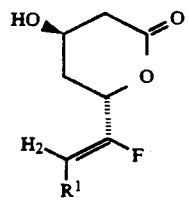

in which $R^1$ has the specified meaning.

The conversion of compounds of the formula III via compounds of the formula IV into compounds of the formula V is carried out by different variants depending on the circumstances and requirements, such as, for example, 1. reaction of the enolates of achiral acetic esters such as, for example, ethyl or propyl esters, which are prepared with strong bases, preferably LDA, in THF, with aldehydes of the formula III in solvents such as, for example, THF, at temperatures between −78° C. and 0° C., results in racemic compounds of the formula IV in which $R^{17}$ denotes an achiral acid protecting group such as, for example, the ethyl or propyl group. Reaction with another acetic ester enolate in solvents such as, for example, THF at −78° C. to room temperature results in racemic compounds of the formula V.

2. Reaction of aldehydes of the formula III with lithium, sodium, potassium or magnesium enolates of optically active acetic esters in solvents such as THF at −78° C. to 0° C. results in optically active compounds of the formula IV. $R^{17}$ in this case denotes a suitable optically active acid protecting group which determines the stereochemistry at C-3. The group preferably used for this is

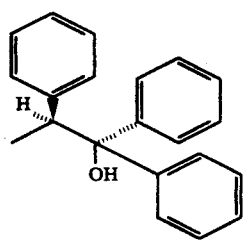

which, according to M. Braun and R. Devant (Tetrahedron Lett. 25, 5031 (1984)) yields the 3R configuration and is prepared from L-(+)-mandelic acid. However, other chiral optically active groups are also suitable. The compounds of the formula IV, which are now optically active, are converted with achiral acetic ester enolates according to variant 1 either directly into the compounds of the formula V, which are now optically active, or after previous conversion into the appropriate alkyl esters, preferably methyl esters.

The conversion of compounds of the formula V into compounds of the formula I is carried out, for example, in analogy to a process known from the literature (K. Narasaka and H. C. Pai, Chemistry Lett. 1980 1415). Initial reaction is with a trialkylborane, preferably triethylborane, in THF at room temperature, followed by reduction at −78° C. to 0° C. with sodium borohydride, where appropriate with the addition of methanol. The stereochemical relationships specified in formula I (syn. 3,5-dihydroxy) are obtained in this way.

The compounds of the formulae I and II obtained by variant 1 can, where appropriate, be separated into the pure enantiomers by the known processes of racemate resolution. The salts and acids of the compounds of the general formula I are obtained by generally known methods.

The lactones of the formula II are likewise obtained by known processes, for example by elimination of water, from the open dihydroxy carboxylic acids of the formula I, $R^2$=H, in benzene, hexane or toluene with addition of p-toluenesulfonic acid or trifluoroacetic acid at room temperature to the reflux temperature.

The aldehydes of the formula III can be prepared from the compounds of the general formula VI

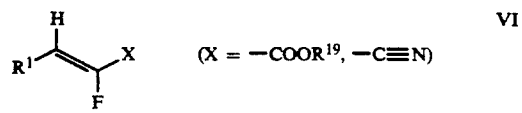

where X is a nitrile group or an ester group, in a variety of ways:

a) reaction of the nitriles of the formula VI (X=—C≡N), in which $R^1$ has the meaning specified for formula I with diisobutylaluminum hydride (DIBAH) in THF at −10° C. to 50° results, after hydrolysis, immediately in the aldehydes of the formula III.

b) Reaction of the carboxylic esters of the formula VI (X=—COOR$^{19}$) in which $R^1$ has the meaning specified for formula I, and $R^{19}$ is alkyl having 1–8 carbon atoms, results, by reduction with DIBAH in THF at −10° C. to 50° C., initially in the corresponding alcohols of the formula VII

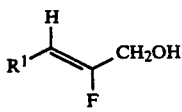   VII in which $R^1$ has the meaning specified for formula I. The alcohols VII can be converted into the aldehydes of the formula III by oxidation with customary oxidizing agents such as chromium(VI) oxide, Swern's reagent (oxalyl chloride/DMSO/NEt$_3$), CrO$_3$.Pyr, manganese dioxide, or by the method of K. B. Sharpless et al., Tetrahedron Lett. 29, 2503 (1976) with N-methylmorpholine/(PPh$_3$)$_3$RuCl$_2$ in customary solvents such as, for example, CH$_2$Cl$_2$ or acetone at temperatures between −50° C. and +30° C.

The compounds of the formula VI (X=—COOR$^{19}$, —C≡N) are obtained from the aldehydes of the formula VIII $R^1$—CH=O   VIII in which $R^1$ has the meaning specified for formula I, specifically by reaction with the phosphonates of the general formula IX

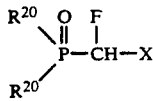   IX in which $R^{20}$ denotes an alkoxy group having 1–6 carbon atoms or a phenyl group which can be substituted 1 to 3 times by halogen or alkoxy having 1–5 carbon atoms, and X has the meaning specified for formula VI, by the Horner-Emmons-Wittig method (Horner et al. Chem. Ber. 91, 61 (1958)).

The reaction is preferably carried out in solvents such as dimethoxyethane or THF in the presence of a base such as, for example, sodium hydride or BuLi at temperatures between −20° C. and room temperature. The predominant products are the E isomers which can be purified, where appropriate, by crystallization or chromatography.

The phosphonates of the formula IX are obtained by processes known from the literature, for example by the method of G. Etemad-Moghadam, J. Seyden-Penne, Bull. Soc. France 3, 448 (1985) or EP-A No. 224,417, H. Machleidt, R. Wessendorf, Liebigs Ann. Chem. 674, 1 (1964).

The aldehydes of the formula VIII are obtained by oxidation with customary oxidizing agents such as, for example, chromium(VI) oxide, Swern's reagent or CrO$_3$.Pyr in customary solvents such as, for example, CH$_2$Cl$_2$, acetone etc. at temperatures between −50° C. and +30° C. from the alcohols of the general formula X $R^1$—CH$_2$OH   X in which $R^1$ has the meaning specified for formula I. The alcohol of the general formula X is prepared by processes described in the literature, as is evident from the table which follows. The aldehydes VIII are obtained directly in accordance with citations (3), (8) and (9).

| Preparation of the alcohols X | | |
|---|---|---|
| $R^1$ | $R^1$—CH$_2$OH   X | |
|  | | German Offenlegungsschrift 38 23 045 (1) (corresponding to EP-A 0,307,342; U.S. Pat. Application Ser. No.: 216 458) |
| | | German Patent Application P 38 00 785.1 (2) (corresponding to U.S. Pat. Application Ser. No.: 294 096) |
| | | Preparation of the aldehydes $R^1$—CH=O VIII: G.E. Stokker et al. J. Med. Chem. 29, 173 (1986) (3) (another method for the preparation of the aldehydes is described in Example 1 f). |
| | | Preparation of the correspondingly substituted alcohols X by reduction of the appropriate carboxylic esters with LiAlH$_4$, DIBAH or AlH$_3$ is described: |
| | | a) for example for G-E equal to S-C: J.M. Spragur et al., J. Am. Chem. Soc. 56 (1934) 2665 (4); Heterocyclic Compounds Vol. 44, Part 1, Thiophene and Derivatives, J. Wiley & Sons, N.Y. 1985, especially page 197 (5); |
| | | b) for G-E equal to C-S: S. Gronowitz et al., Acta pharm. sued. 9 (1972) 301 (6); |
| | | c) for G-E equal to C-O: F. Boberg et al., Liebigs Ann. Chem. 1984, 233 (7) |
| | | d) for G-E equal to C-N: European Patent Application A 0,221,025 (8) or by analogous methods. German Offenlegungsschrift 37 22 806 (9) (corresponding to EP-A 0,300,249; U.S. Pat. Application Ser. No.: 216 423) and European Patent Application A 0,221,025 (8) propose another process for the preparation of appropriately substituted aldehydes VIII. |
| | | German Offenlegungsschrift 37 22 807 (10) (corresponding to EP-A 0,306,649; U.S. Pat. Application Ser. No.: 216 331). |

Intermediates are purified where necessary by distillation, crystallization, flash chromatography or HPLC.

Besides the compounds described in the examples, the following compounds can be prepared by the process according to the invention:

Z-6-(S)-2-[(6-(4-fluorophenyl)-4-isopropyl-3-phenyl-pyridazin-5-yl)]-(1-fluoro-2-ethenyl)-4(R)-hydroxy-3,4,5,6-tetrahydro-2H-pyran-2-one Z-6-(S)-2-[(4-(4-fluorophenyl)-3,6-bis-isopropyl-pyridazin-5-yl)]-(1-fluoro-2-ethenyl)-4(R)-hydroxy-3,4,5,6-tetrahydro-2H-pyran-2-one Z-6-(S)-2-[(6-tert.-butyl-4-(4-fluorophenyl)-3-phenyl-pyridazin-5-yl)]-(1-fluoro-2-ethenyl)-4(R)-hydroxy-3,4,5,6-tetrahydro-2H-pyran-2-one 1Z, 3E, 6(S)-[1-fluoro-3-isopropyl-4-(4-fluoro-3-methyl-phenyl)-4-(3,5-dimethyl-2-methoxyphenyl)-butadienyl]-4(R)-hydroxy-3,4,5,6-tetrahydro-2H-pyran-2-one 1Z,3E,6(S)-[1-fluoro-3-isobutyl-4,4-di-(4-fluorophenyl)]-4-(R)-hydroxy-3,4,5,6-tetrahydro-2H-pyran-2-one Z-6(S)-2-[2-isopropyl-4-phenyl-6-(4-fluorophenyl)-phenyl](1-fluoro-2-ethenyl)-4-(R)-hydroxy-3,4,5,6-tetrahydro-2H-pyran-2-one Z-6(S)-2-[1-cyclohexyl-2-isopropyl-4-(4-fluorophenyl)-1H-pyrrol-3-yl]-(1-fluoro-2-ethenyl)-4(R)-hydroxy-3,4,5,6-tetrahydro-2H-pyran-2-one Z-6(S)-(2-(4,6-bis-(4-fluorophenyl)-2-(1-methylethyl)-pyridin-3-yl)-1-fluoroethenyl)-4-(R)-hydroxy-3,4,5,6-tetrahydro-2H-pyran-2-one Z-6(S)-(1-fluoro-2-(4-(4-fluorophenyl)-2-(1-methylethyl)-6-phenylpyridin-3-yl)-ethenyl)-4-(R)-hydroxy-3,4,5,6-tetrahydro-2H-pyran-2-one t-butyl 6Z-3(R), 5(S)-dihydroxy-7-[2-isopropyl-4-phenyl-6-(4-fluorophenyl)-phenyl]-6-fluoro-heptanoate t-butyl 6Z-3(R), 5(S)-dihydroxy-7-[1-cyclohexyl-2-isopropyl-4-(4-fluorophenyl)-1H-pyrrol-3-yl]-6-fluoro-hept-6-enoate t-butyl 6Z-7-(4,6-bis-(4-fluorophenyl)-2-(1-methylethyl)pyridin-3-yl)-3R, 5S-dihydroxy-6-fluorohept-6-enoate t-butyl 6Z-3(R), 5(S)-dihydroxy-6-fluoro-7-(4-(4-fluorophenyl)-2-(1-methylethyl)-6-phenylpyridin-3-yl)-hept-6-enoate tert.-butyl 6Z-3(R), 5(S)-dihydroxy-6-fluoro-7-[6-(4-fluorophenyl)-4-isopropyl-3-phenyl-pyridazin-5-yl]-hept-6-ene-carboxylate tert.-butyl 6Z-3(R), 5(S)-dihydroxy-6-fluoro-7-[4-(4-fluorophenyl)-3,6-bis-isopropyl-pyridazin-5-yl]-hept-6-enecarboxylate tert.-butyl 6Z-3(R), 5(S)-dihydroxy-6-fluoro-7-[6-tert.-butyl-4-(4-fluorophenyl)-3-phenyl-pyridazin-5-yl]-hept-6-ene-carboxylate t-butyl 6Z, 8E, 3(R), 5(S)-dihydroxy-9-(3,5-dimethyl-2-methoxyphenyl)-9-(4-fluoro-3-methylphenyl)-6-fluoro-8-isopropyl-6,8-nonadienoate t-butyl 6Z, 3(R), 5(S)-dihydroxy-9,9-di-(4-fluorophenyl)-6-fluoro-8-isobutyl-6,8-nonadienoate

BIOLOGICAL TEST SYSTEMS

1. HMG CoA reductase activity in enzyme preparations

The HMG-CoA reductase activity was measured on solubilized enzyme preparations from liver microsomes from rats which, after a changeover in the day/night rhythm, had been induced with cholestyramine (®Cuemid).

The substrate used was (S,R) $^{14}$C-HMG-CoA, and the concentration of NADPH was maintained constant during the incubation by a regenerating system. $^{14}$C-Mevalonate was separated from the substrate and other products (e.g. $^{14}$C-HMG) by column elution, with the elution profile of each individual sample being determined.

Permanent inclusion of $^3$H-mevalonate was dispensed with because the determination was for relative data on the inhibitory effect. In each test series the enzyme-free control, the enzyme-containing normal mixture (=100%) and those with added product, final concentration $10^{-5}$ to $10^{-9}$ M, were treated together. Each individual value was formed as the mean of 3 parallel samples. The significance of the differences between means for product-free and product-containing samples was assessed using the t test.

The method described above was used to measure, for example, the following figures for the inhibition of HMG-CoA reductase by the compounds according to the invention [IC$_{50}$/mol/liter means the molar concentration of the compound per liter necessary for 50% inhibition]:

TABLE 1

| Compound of Example | IC$_{50}$/mol/liter |
| --- | --- |
| 10 a | 2.9 × 10$^{-9}$ |
| 10 b | 9.0 × 10$^{-9}$ |
| 10 g | 1.8 × 10$^{-9}$ |

2. Suppression or inhibition of HMG-CoA reductase in cell cultures of HEP-G2 cells Monolayers of HEP-G2 cells in the lipoprotein-free nutrient medium were preincubated with appropriate concentrations of the test substances for a defined time (for example 1 hour) and, after addition of the labeled precursor, for example sodium $^{14}$C-acetate, the incubation was continued (for example for 3 hours). An internal standard ($^3$H-cholesterol) was added and then a portion of the cells underwent alkaline hydrolysis. The lipids from the hydrolyzed cells were extracted with chloroform/methanol. After addition of carrier cholesterol to this lipid mixture it was subjected to preparative thin-layer chromatography, the cholesterol band was visualized with iodine vapor and then isolated, and the amount of $^{14}$C-cholesterol formed from the $^{14}$C-precursor was determined by scintigraphy. Cell protein was determined in an aliquot of the cells so that it is possible to calculate the amount of $^{14}$C-cholesterol formed per unit time and per mg of cell protein. The inhibitory effect of the particular test product on the cholesterol biosynthesis by HEP-G2 cell cultures was obtained by comparing this figure with the amount of $^{14}$C-cholesterol formed per mg of cell protein and unit time in a culture treated in the same way but free of test substance.

Examination of substances for inhibition of cholesterol biosynthesis in confluent cell cultures (monolayers) of HEP-G2 cells 1. Lipoprotein-free medium (DMEM) — 24 h
2. Incubation with test products — 1 h
3. Incubation with $^{14}C$-acetate — 3 h
4. Cytolysis
5. TLC separation of the reaction product $^{14}C$-cholesterol  | Internal standard 3H-cholesterol | Cell protein determination
6. Isolation of the $^{14}C$-cholesterol
7. Scintillation measurement
8. Result in nmol of $^{14}C$-cholesterol/mg of cell protein by comparison with the solvent control The method described above was used to measure, for example, the following figures for the inhibition of cholesterol biosynthesis (in HEP-G2 cells) by the compounds according to the invention (the $IC_{50}$/mol/liter is that concentration of the compound which brings about 50% inhibition of cholesterol biosynthesis) (Tab. 2).

TABLE 2

| Compound of Example | $IC_{50}$/mol/liter |
|---|---|
| 10 a | $1.9 \times 10^{-8}$ |
| 11 a | $1.8 \times 10^{-8}$ |
| 10 g | $2.5 \times 10^{-9}$ |
| 10 b | $4.6 \times 10^{-9}$ |
| 11 b | $2.0 \times 10^{-8}$ |

The compounds of the general formula I and II are distinguished by strongly inhibiting HMG-CoA reductase, the rate-determining enzyme of cholesterol biosynthesis.

The extent of the inhibition by compounds of the general formula I and II, which is characterized by $IC_{50}$ values in the range $10^{-7}$ to $10^{-9}$ mol per liter, is distinctly higher than for completely synthetic HMG-CoA reductase inhibitors known from the literature, such as, for example, those described by G. E. Stokker et al., J. Med. Chem. 29, 170 (1986).

The enzyme HMG-CoA reductase is widespread in nature. It catalyzes the formation of mevalonic acid from HMG-CoA. This reaction is a central step in cholesterol biosynthesis (cf. J. R. Sabine in CRC Series in Enzyme Biology: 3-Hydroxy-3-methylglutaryl Coenzyme A Reductase, CRC Press Inc. Boca Raten, Fla. 1983 (ISBN 0-8493-6551-1)).

High cholesterol levels are thought to be associated with a number of diseases such as, for example, coronary heart diseases or arteriosclerosis. This is why lowering elevated cholesterol levels is an aim of therapy for preventing and treating such diseases.

One approach to this comprises inhibiting or reducing endogenous cholesterol biosynthesis. Inhibitors of HMG-CoA reductase block cholesterol biosynthesis at an early stage.

The compounds of the general formula I and II are therefore suitable as hypolipidemics and for the treatment and prophylaxis of arteriosclerotic changes.

The invention therefore also relates to pharmaceutical products based on these compounds, and to the use thereof as medicinal agents, especially as hypolipidemics and for the prophylaxis of arteriosclerotic changes.

The compounds of the formula I and II are used as hypolipidemics or anti-arteriosclerotics in oral doses of 3 to 2500 mg per day, but preferably in the dose range 10–500 mg. These daily doses can also, if required, be divided into two to four individual doses or administered in depot form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. Excretion of bile acids results in increased de novo synthesis and thus in increased breakdown of cholesterol (cf. M. S. Brown, P. T. Koranen and J. C. Goldstein, Science 212, 628 (1981); M. S. Brown, J. C. Goldstein, Spektrum der Wissenschaft 1985, 1, 96).

The compounds of the formula I according to the invention can be used in the form of the esters, as free acids or in the form of the physiologically acceptable inorganic or organic salts thereof. The compounds of the formula I and II can be used in the form of the aqueous solutions or suspensions thereof, or else dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, or else polyethers such as, for example, polyethylene glycol, or else in the presence of other pharmacologically acceptable polymeric vehicles such as, for example, polyvinylpyrrolidone, or in solid compositions.

Preferred for the compound of the formula I or II are solid presentations which can be administered orally and which can contain the customary auxiliaries. They are prepared by customary methods.

Particularly suitable as composition for oral use are tablets, coated tablets or capsules. One dosage unit preferably contains 10 to 500 mg of active substance.

The compounds of the formula III, IV, V, VI and VII are new and represent valuable intermediates for the preparation of compounds of the formula I. The invention therefore also relates to these compounds and to processes for the preparation thereof.

Preliminary note: Unless indicated otherwise, NMR spectra were recorded in $CDCl_3$ with TMS as internal standard. The following abbreviations are used to classify NMR signals: s=singlet, brs=broad singlet, d=doublet, t=triplet, q=quartet, h=heptet, mc=centered multiplet, m=multiplet.

Melting points are uncorrected.

The following abbreviations are used for substituents: i=iso, t=tertiary, c=cyclo.

EXAMPLE 1

General Procedure For The Preparation Of Compounds Of The General Formula VIII

Example 1a 4,6-Bis(4-fluorophenyl)-2-(1-methylethyl)-pyrimidine-3-aldehyde 12 g (0.12 mole) of $CrO_3$ are suspended in 400 ml of abs. $CH_2Cl_2$ by stirring under argon. After 15 min, the mixture is cooled to 0° C. and a solution of 19.4 ml (0.24 mol) of pyridine in 100 ml of abs. $CH_2Cl_2$ is added dropwise. The mixture is then allowed to warm to room temperature while stirring, and 8 g (24 mmol) of 3-hydroxy-4,6-bis(4-fluorophenyl)-2-(1-methylethyl)-pyrimidine (formula X, prepared as described in German patent application no. P 38 23 045.3) are added dropwise. The mixture is stirred at room temperature for 2 h. After the reaction is complete, the methylene chloride phase is decanted off and concentrated in vacuo, and the residue is purified by flash chromatography ($CH_2Cl_2$) on silica gel.

Yield: 7.2 g (89% of theory) of pale crystals.
melting point 119°–122° C. of VIIIa.
$R_f$=0.84 (cyclohexane/ethyl acetate=2:1).
$^1$H NMR: δ values in ppm 1.4 (d, 6H, $CH_3$), 4.0 (h, 1H, CH), 7.0–7.9 (m, 6H, aromat. prot.), 8.5–8.9 (m, 2H, aromat. prot.), 10.1 (s, 1H, CH=O).
MS: m/e=338 $C_{20}H_{16}F_2N_2O$.

Example 1b–1l

The compounds VIII b–VIII l were prepared in a manner analogous to that described in Example 1a (cf. Tab. 1).

The aromatic aldehydes VIII f and VIII l can also be prepared as described in Example 1f.

Example 1f

2-Isopropyl-4,6-bis-(4-fluorophenyl)-benzaldehyde VIII f 4.17 g (9 mmol) of the palladium complex

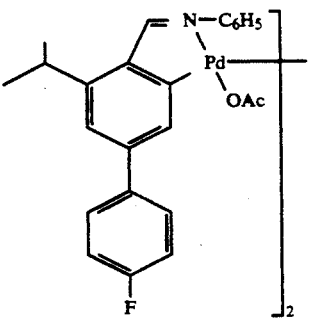

(prepared in analogy to the description in the review by R. F. Heck, Palladium Reagents in Organic Synthesis, Academic Press 1985, page 290–94) in 100 ml of abs. toluene are mixed with 18.9 g (72 mmol) of triphenylphosphine at room temperature, and the mixture is stirred for 30 min. A Grignard solution prepared from 0.875 g (36 mmol) of magnesium turnings, 60 ml of abs. diethyl ether and 7.0 g (40 mmol) of 4-bromofluorobenzene is added dropwise at 20° C. within 2 min. The mixture is then stirred at room temperature for 15 min and neutralized with 50% concentrated hydrochloric acid. The org. phase is separated off, dried and concentrated in vacuo. The residue is filtered through silica gel by cyclohexane/toluene=10:1. The aldehyde VIII f is obtained.

Yield: 2.31 g (80.6% of theory) melting point 110°–112° C. $R_f$=0.4 (cyclohexane/toluene 1:1).
$^1$H NMR: δ values in ppm 1.4 (d, 6H, $CH_3$), 4.0 (h, 1H, CH), 7.0–7.9 (m, 8H, aromat. prot.), 10.0 (s, 1H, CH=O).
MS: m/e=336 $C_{22}H_{18}F_2O$.

TABLE 1

| Example | Compound | $R^1$ | Yield % | $R_f$ m.p. °C. | $^1$H NMR δ/ppm = MS: m/e = |
|---|---|---|---|---|---|
| 1 a | VIIIa | | 89% | | cf. description Example 1a |

TABLE 1-continued

VIII

| Example | Compound | R¹ | Yield % | R_f m.p. °C. | ¹H NMR δ/ppm = MS: m/e = |
|---|---|---|---|---|---|
| b | VIIIb | [2-phenyl-4-(4-fluorophenyl)-5-methyl-6-isopropylpyridin-3-yl] | 82.5% | m.p. 104° | C₂₁H₁₈FNO (319) |
| c | VIIIc | [1,1-bis(3-methyl-4-fluorophenyl)-2-methyl-3-methylbut-1-en-1-yl] | 79.4% | m.p. 72–73° | C₂₀H₂₀F₂O (314) |
| d | VIIId | [3-(4-fluorophenyl)-4-(4-fluorophenyl)-5-methyl-6-isopropylpyridazin-3-yl] | 81.2% | m.p. 136° | C₂₀H₁₆F₂N₂O (338) |
| e | VIIIe | [4-(4-fluorophenyl)-3-methyl-2-isopropyl-1-phenylpyrrol-3-yl] | 78.8% | m.p. 122° | C₂₀J₁₈FNO (307) |
| f | VIIIf | [5-(4-fluorophenyl)-3-(4-fluorophenyl)-2-methyl-6-isopropylbiphenyl] | 80.6 | | cf. description Example 1f |

TABLE 1-continued
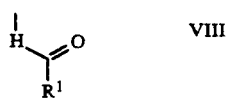
VIII
| Example | Compound | R¹ | Yield % | $R_f$ m.p. °C. | ¹H NMR δ/ppm = MS: m/e = |
|---|---|---|---|---|---|
| g | VIIIg | | 73% | m.p. 61° C. | $C_{17}H_{17}FN_2O$ (284) |
| h | VIIIh | | 69% | pale oil | $C_{21}H_{17}F_2NO$ (337) |
| i | VIIIi | | 89.2% | m.p. 87–88° C. | $C_{18}H_{16}F_2O$ (286) |
| j | VIIIj | | 72% | pale oil | $C_{18}H_{21}FN_2O$ (300) |
| k | VIIIk | | 82% | m.p. 119–120° C. | $C_{17}H_{20}FNO$ (273) |

TABLE 1-continued

| Example | Compound | R[1] | Yield % | R_f m.p. °C. | $^1$H NMR δ/ppm = MS: m/e = |
|---|---|---|---|---|---|
| 1 | VIIIl |  | 94% | yellow oil | $C_{19}H_{21}FO$ (284) |

EXAMPLE 2

General Procedure For The Preparation Of Compounds Of The General Formula VI (X=CO$_2$R$^{19}$)

Example 2a

Ethyl 2Z-2-fluoro-3-[4,6-bis-(4-fluorophenyl)-2-(1-methyle-thyl)-pyrimidin-3-yl]-acrylate 8.06 g (0.022 mole) of ethyl phosphinoxy-fluoroacetate (formula IX, R$^{20}$=C$_6$H$_5$, X=CO$_2$Et; prepared as described by G. Etemad-Moghadam and J. Seyden-Penne in Bull. Soc. Chim. France 3, 448–454 (1985)) are dissolved in 180 ml of abs. THF under argon. 15 ml (24 mmol) of a solution of butyllithium in hexane are added dropwise to this solution while stirring at 0° C. After stirring for 30 min, 7.6 g (22.4 mmol) of 4,6-bis-(4-fluorophenyl)-2-(1-methylethyl)-pyrimidine-3-aldehyde (from Example 1a dissolved in 10 ml of abs. THF are added dropwise at room temperature. The reaction is complete after about 3 h. 200 ml of diethyl ether are added, and the mixture is extracted 2× with saturated sodium chloride solution. The org. phase is separated off, dried with MgSO$_4$, filtered and concentrated in vacuo.

Yield: 7.8 g (75% of theory) of pale crystals.
melting point 85°–89° C. of VIa.
R$_f$=0.52 (cyclohexane/ethyl acetate=10:1).
$^1$H NMR: δ values in ppm 1.35 (t, 3H, CH$_3$), 1.40 (d, 6H, CH$_3$), 3.2 (m, 1H, CH), 4.4 (q, 2H, OCH$_2$CH$_3$), 7.12 (d, J=33Hz, 1H, CH=CF—), 7.1–7.2 (m, 4H, aromat prot.), 7.7 and 8.6 (m, 2+2H, aromat prot.).
MS: m/e=426 C$_{24}$H$_{21}$F$_3$N$_2$O$_2$.

Example 2a-2l

The compounds VI b–VI l were prepared in a manner analogous to that described in Example 2a (cf. Tab. 2).

EXAMPLE 3

General Procedure For The Preparation Of Compounds Of The General Formula VI (X=CN)

Example 3a

2-Fluoro-3-[4,6-bis-(4-fluorophenyl)-2-(1-methylethyl)-pyrimidin-3-yl]-acrylonitrile 0.28 g (6 mmol) of sodium hydride 55% suspension in oil is suspended in 20 ml of abs. DME. While stirring, 1.17 g (0.95 ml, 6 mmol) of 2-(O,O-diethylphosphono)-2-fluoroacetonitrile (formula IX, R$^{20}$=OC$_2$H$_5$, X=C≡N; prepared as described in EP-A No. 224,417) are added dropwise, and the mixture is stirred for 15 min. Then 1.6 g (5 mmol) of 4,6-bis-(4-fluorophenyl)-2-(1-methylethyl)-pyrimidine-3-aldehyde from Example 1a are added dropwise. After 1 h the reaction mixture is adjusted to pH 7 with 2 N hydrochloric acid and concentrated in vacuo. The residue is mixed with 200 ml of EA/H$_2$O in the ratio 1:1, and the ethyl acetate phase is separated off, washed 2× with saturated sodium chloride solution, dried, filtered and concentrated in vacuo, and the residue is purified on a silica gel column (cyclohexane/ethyl acetate=10:1)

Yield: 1.6 g (72% of theory) of yellow crystals.
melting point 112° C. VIa', X=CN.
R$_f$=0.49 (Z isomer) cyclohexane/ethyl acetate=10:1.
$^1$H NMR: δ values in ppm 1.4 (d, 6H, CH$_3$), 3.18 (m, 1H, CH), 6.78 (d, 1H, J=32 Hz, CH=CF), 7.2–8.5 (m, 8H, aromat. Prot.).
MS: m/e=361 C$_{22}$H$_{17}$F$_2$N$_3$.

Example 3b-3l

The compounds VI b'–VI l' (X=CN) can be prepared in a manner analogous to that described in Example 3a.

TABLE 2
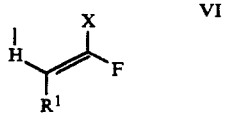
(X = CO₂Et)
| Example | Compound | R¹ | Yield % | $R_f$(Z)<br>m.p. °C. (Z) | ¹H NMR δ/ppm =<br>MS: m/e = |
|---|---|---|---|---|---|
| 2a | VIa | 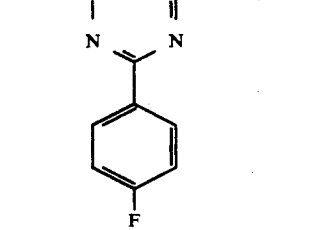 | 75% | m.p. 89° | cf. description Example 2a |
| 2b | VIb | 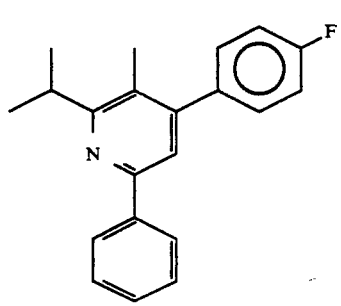 | 81% | $R_f$=0.55 | C₂₅H₂₃NF₂O₂ (407) |
| 2c | VIc | 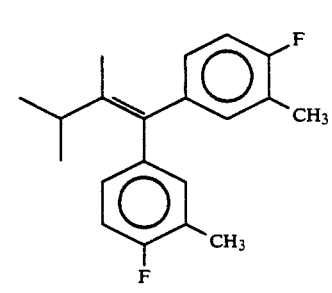 | 63% | $R_f$=0.59 | C₂₄H₂₅F₃O₂ (402) |
| 2d | VId | 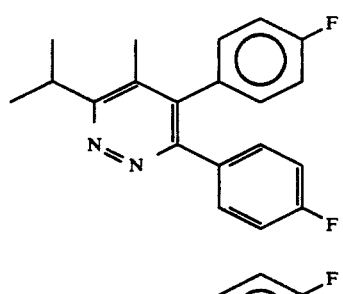 | 74% | $R_f$=0.46 | C₂₄H₂₁F₃N₂O₂ (426) |
| 2e | VIe | 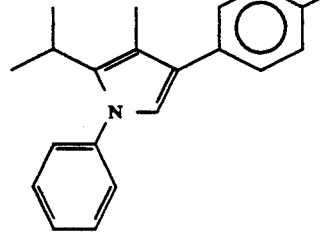 | 84% | $R_f$=0.49 | C₂₄H₂₃NF₂O₂ (395) |

TABLE 2-continued $$\underset{R^1}{\overset{H}{\text{C}}}=\underset{F}{\overset{X}{\text{C}}} \quad VI$$

(X = CO₂Et)

| Example | Compound | R¹ | Yield % | R_f(Z) m.p. °C. (Z) | ¹H NMR δ/ppm = MS: m/e = |
|---|---|---|---|---|---|
| 2f | VIf | 4'-fluoro-3-isopropyl-5-methyl-[1,1':3',1''-terphenyl]-yl (with 4-fluorophenyl) | 73% | R_f=0.51 | C₂₆H₂₃F₂O₂ (424) |
| 2g | VIg | 2-isopropyl-5-(4-fluorophenyl)-4-methyl-6-isopropylpyrimidin-yl | 71% | R_f=0.57 | C₂₁H₂₂N₂F₂O₂ (372) |
| 2h | VIh | 2-(4-fluorophenyl)-4-(4-fluorophenyl)-5-methyl-6-isopropylpyridin-yl | 69% | R_f=0.55 | C₂₅H₂₂F₃NO₂ (425) |
| 2i | VIi | 1-(4-fluorophenyl)-3-methyl-4-methyl-1-(4-fluorophenyl)but-1-en-yl | 84% | R_f=0.48 | C₂₂H₂₁F₃O₂ (374) |
| 2j | VIj | 3-tert-butyl-6-isopropyl-5-methyl-4-(4-fluorophenyl)pyridazin-yl | 57% | R_f=0.52 | C₂₂H₂₆F₂N₂O₂ (388) |

TABLE 2-continued

VI: H−C(X)=C(F)(R¹), with X substituent above (X = CO₂Et)

| Example | Compound | R¹ | Yield % | $R_f$(Z) m.p. °C. (Z) | ¹H NMR δ/ppm = MS: m/e = |
|---|---|---|---|---|---|
| 2k | VIk | 1-isopropyl-2-isopropyl-3-methyl-4-(4-fluorophenyl)-pyrrol-4-yl | 63% | $R_f$=0.51 | $C_{21}H_{25}NF_2O_2$ (361) |
| 2l | VIl | 2-methyl-3,5-diisopropyl-4'-fluoro-biphenyl-yl | 71% | $R_f$=0.49 | $C_{23}H_{26}F_2O_2$ (372) |

EXAMPLE 4

General Procedure For The Preparation Of Compounds Of The General Formula VII

Example 4a 2Z-1-Hydroxy-3-fluoro-3-[4,6-bis-(4-fluorophenyl)-2-(1-methylethyl)-pyrimidin-3-yl]-2-propene 12.1 g (28.6 mmol) of ethyl 2Z-2-fluoro-3-[4,6-bis-(4-fluorophenyl)-2-(1-methylethyl)-pyrimidin-3-yl]-acrylate (Example 2a) are dissolved in 200 ml of abs. $CH_2Cl_2$ and, at 0° C., 52.4 ml (62.4 mmol) of diisobutylaluminum hydride are added dropwise under argon. The mixture is stirred at room temperature for 2 h. After the reaction is complete, the excess reagent is decomposed with 10 ml of isopropanol, and then 30 ml of water are added, and the mixture is stirred for about ¼ hour and filtered through a clarifying layer to remove precipitated aluminum salts. The filtrate is dried with $MgSO_4$, filtered and concentrated. Column chromatography on silica gel (cyclohexane/ethyl acetate=4:1) yields the title compound.

Yield: 9.8 g of white crystals (90% of theory) of VIIa.

melting point 112°–114° C.

$R_f$=0.2 (cyclohexane/ethyl acetate=2:1)

¹H NMR: δ values in ppm. 1.38 (d, 6H, $CH_3$), 1.5 (s, 1H, OH), 3.28 (h, 1H, CH), 4.2 (dd, 2H J=12 Hz, $CH_2OH$), 5.92 (d, 1H J=36 Hz,

Z

CH=CF), 7.1–7.2 (m, 4H, aromat. prot.), 8.55–8.65 (m, 2H, aromat. prot.).

E isomer: 3.7 (dd, 2H, J=20 Hz, $CH_2OH$), 6.35 (d, 1H J=16 Hz,

E

CH=CF)

MS: m/e 384 $C_{22}H_{19}ON_2F_3$.

EXAMPLE 4b–4l

The compounds VIIb-VII l were prepared in a manner analogous to that described in Example 4a (cf. Tab. 3).

TABLE 3

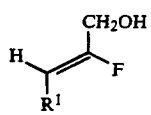

VII

| Example | Compound | R¹ | Yield % | $R_f$(Z) m.p. °C. (Z) | ¹H NMR δ/ppm = MS: m/e = |
|---|---|---|---|---|---|
| 4a | VIIa | 4-methyl-6-isopropyl-2-(4-fluorophenyl)pyrimidine with 4-fluorophenyl | 90% | | cf. description Example 4a |
| 4b | VIIb | 4-methyl-6-isopropyl-2-phenyl-pyridine with 4-fluorophenyl | 87% | $R_f$=0.25 | $C_{23}H_{21}F_2NO$ (365) |
| 4c | VIIc | isopropyl, methyl, bis(4-fluoro-3-methylphenyl) substituted alkene | 63% | $R_f$=0.42 | $C_{22}H_{23}FO$ (360) |
| 4d | VIId | 4-methyl-6-isopropyl-3-(4-fluorophenyl)pyridazine with 4-fluorophenyl | 62% | $R_f$=0.21 | $C_{22}H_{19}F_3N_2O$ (384) |
| 4e | VIIe | 3-methyl-2-isopropyl-1-phenylpyrrole with 4-fluorophenyl | 83% | $R_f$=0.27 | $C_{22}H_{21}NFO$ (353) |

TABLE 3-continued $$\underset{R^1}{H}C=C\underset{F}{CH_2OH} \quad VII$$

| Example | Compound | R¹ | Yield % | R_f (Z) m.p. °C. (Z) | ¹H NMR δ/ppm = MS: m/e = |
|---|---|---|---|---|---|
| 4f | VIIf | (3,5-disubstituted phenyl: 4-fluorophenyl and 4-fluorobiphenyl with isopropyl and methyl) | 78% | R_f = 0.31 | C₂₄H₂₁F₃O (382) |
| 4g | VIIg | (pyrimidine with isopropyl, methyl, 4-fluorophenyl, and isopropyl) | 62% | R_f = 0.32 | C₁₉H₂₀N₂F₂O (330) |
| 4h | VIIh | (pyridine with isopropyl, methyl, 4-fluorophenyl, and 4-fluorophenyl) | 74% | R_f = 0.26 | C₂₃H₂₀F₃NO (383) |
| 4i | VIIi | (alkene with isopropyl, methyl, 4-fluorophenyl, and 4-fluorophenyl) | 82% | R_f = 0.40 | C₂₀H₁₉F₃O (332) |
| 4j | VIIj | (pyridazine with isopropyl, methyl, 4-fluorophenyl, and tert-butyl) | 67% | R_f = 0.29 | C₂₀H₂₄F₂N₂O (246) |

TABLE 3-continued

Structure VII:
- CH₂OH group, H, F, and R¹ on a propene backbone

| Example | Compound | R¹ | Yield % | $R_f$(Z) m.p. °C. (Z) | $^1$H NMR δ/ppm = MS: m/e = |
|---|---|---|---|---|---|
| 4k | VIIk | 2-isopropyl-3-methyl-5-(4-fluorophenyl)-1-isopropyl-pyrrole | 49% | $R_f$=0.32 | $C_{19}H_{23}NF_2O$ (319) |
| 4l | VIIl | 4'-fluoro-2-methyl-3,5-diisopropyl-biphenyl | 81% | $R_f$=0.35 | $C_{21}H_{24}F_2O$ (330) |

EXAMPLE 5

General Procedure For The Preparation Of Compounds Of The General Formula III

Example 5a (variant A)

2Z-2-Fluoro-3-[4,6-bis-(4-fluorophenyl)-2-(1-methylethyl)-pyrimidin-3-yl]-propene-2-aldehyde 11.3 g (97 mmol) of N-methyl-morpholine N-oxide 97% pure (Fluka) are dissolved in 150 ml of abs. acetone. 0.9 g (0.97 mmol) of tris-(triphenylphosphine)-ruthenium(I) chloride (Fluka) is added while stirring at 20° C. Subsequently, 9.3 g (24.2 mmol) of 2Z-1-hydroxy-2-fluoro-3-[4,6-bis-(4-fluorophenyl)-2-(1-methylethyl)-pyrimidin-3-yl]-2-propene (Example 4a) in 150 ml of abs. acetone are added dropwise. The mixture is stirred at room temperature for 20 h. The solvent is removed in vacuo, and the residue is filtered through silica gel (diethyl ether containing 1% NEt₃)

Yield: 6.4 g (67.5% of theory) of white crystals IIIa. Melting point 159°-162° C.

$R_f$=0.89 (cyclohexane/ethyl acetate=1:1).

$^1$H NMR: δ values in ppm: 1.38 (d, 6H, CH₃), 3.15 (h, 1H, CH), 6.9 (d, 1H, J=34 Hz, $$\overset{Z}{CH=CF),}$$

7.1–7.25 (m, 8H, aromat. prot.), 7.6–7.7 (m, 2H, aromat. prot.), 8.55–8.65 (m, 2H, aromat. prot.), 9.4 (d, 1H J=16 Hz, CH=O).

MS: m/e 382 $C_{22}H_{17}N_2F_3O$.

Example 5b–5l

The compounds III b–III l were prepared in a manner analogous to that described in Example 5a (cf. Tab. 4).

The compounds III a–III l can also be obtained by variant B, as described in Example 5a which follows.

Example 5a' (variant B)

2Z-2-Fluoro-3-[4,6-bis-(4-fluorophenyl-2-(1-methylethyl)pyrimidin-3-yl]-propene-2-aldehyde 7.2 g (20 mmol) of 2-fluoro-3-[4,6-bis-(4-fluorophenyl)-2-(1-methylethyl)-pyrimidin-3-yl]-acrylonitrile (Example 3a) are dissolved in 150 ml of abs. THF. At −10° C. 35 ml (40 mmol) of diisobutylaluminum hydride (1.2 molar solution in toluene) are added dropwise, and the mixture is stirred for a further 2 h in the cold. The pH is then adjusted to 5–6 with 1 N hydrochloric acid, and the mixture is extracted with ethyl acetate. The combined EA phases are washed free of acid with NaHCO₃, dried with MgSO₄, filtered and concentrated in vacuo. The residue is chromatographed on silica gel (cyclohexane/ethyl acetate=10:1)

Yield: fraction 16–60 3.1 g of IIIa (E isomer) $R_f$=0.45. fraction 61–120 3.1 g of IIIa (Z isomer) $R_f$=0.27.

Melting point=159°-162° C.

$^1$H NMR: Z isomer, identical to Example 5a (variant A) δ=6.92 ppm, J=34 Hz, CH=CF.

$^1$H NMR: E isomer δ=7.31 ppm, J=16 Hz, CH=CF.

TABLE 4
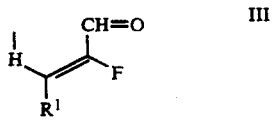
| Example | Compound | R¹ | Yield % | $R_f$(Z) m.p. °C. (Z) | ¹H NMR δ/ppm = MS: m/e = |
|---|---|---|---|---|---|
| 5a | IIIa | | 67.5% | cf. description Example 5a | |
| 5b | IIIb | | 62.4% | $R_f$=0.82 | $C_{23}H_{19}F_2NO$ (363) |
| 5c | IIIc | | 82% | $R_f$=0.92 | $C_{11}H_{21}F_2O$ (358) |
| 5d | IIId | | 71% | $R_f$=0.69 | $C_{22}H_{17}F_3N_2O$ (382) |
| 5e | IIIe | | 89% | $R_f$=0.80 | $C_{22}H_{19}NFO$ (357) |

TABLE 4-continued

III $$\underset{R^1}{\overset{H}{\diagdown}}C=C\underset{F}{\overset{CH=O}{\diagup}}$$

| Example | Compound | R¹ | Yield % | $R_f$(Z)<br>m.p. °C. (Z) | ¹H NMR δ/ppm =<br>MS: m/e = |
|---|---|---|---|---|---|
| 5f | IIIf | (3,5-diaryl with isopropyl, methyl, 4-fluorophenyl, 4-fluorophenyl) | 87% | $R_f$=0.78 | $C_{24}H_{19}F_3O$ (380) |
| 5g | IIIg | (pyrimidine with isopropyl, methyl, 4-fluorophenyl, isopropyl) | 83% | $R_f$=0.90 | $C_{19}H_{18}N_2F_2O$ (328) |
| 5h | IIIh | (pyridine with isopropyl, methyl, 4-fluorophenyl, 4-fluorophenyl) | 95% | $R_f$=0.82 | $C_{23}H_{18}F_3NO$ (381) |
| 5i | IIIi | (alkene with isopropyl, methyl, 4-fluorophenyl, 4-fluorophenyl) | 91% | $R_f$=0.95 | $C_{20}H_{17}F_3O$ (330) |
| 5j | IIIj | (pyridazine with isopropyl, methyl, 4-fluorophenyl, t-butyl) | 78% | $R_f$=0.70 | $C_{20}H_{22}F_2N_2O$ (344) |

TABLE 4-continued

| Example | Compound | R¹ | Yield % | $R_f$(Z) m.p. °C. (Z) | $^1$H NMR δ/ppm = MS: m/e = |
|---|---|---|---|---|---|
| 5k | IIIk | (2-methyl-1-isopropyl-pyrrol-3-yl with 4-fluorophenyl) | 81% | $R_f$=0.85 | $C_{19}H_{21}NF_2O$ (317) |
| 5l | IIIl | (2,6-diisopropyl-4'-fluorobiphenyl) | 64% | $R_f$=0.9 | $C_{21}H_{22}F_2O$ (328) |

EXAMPLE 6

General Procedure For The Preparation Of Compounds Of The General Formula IV With $R^{17}=$

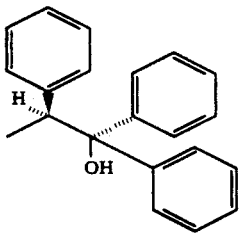

Example 6a 4Z-3(S)-Hydroxy-4-fluoro-5-[4,6-bis-(4-fluorophenyl)-2-(1-methylethyl)-pyrimidin-3-yl]-pent-4-ene-carboxylic acid 2(S)-hytra ester
(hytra=2-hydroxy-1,2,2-triphenylacetate)

9.3 ml of butyllithium (13.5 mmol) are added dropwise to 1.5 g (2.1 ml, 13.5 mmol) of abs. diisopropylamine in 33 ml of abs. THF while stirring at 0° C. The mixture is then stirred at 0° C. for 20 min. Then 2.21 g (6.6 mmol) of (S)(−)-2-hydroxy-1,2,2-triphenylacetate (Merck-Schuchardt) suspended in 50 ml of abs. THF are added dropwise at −70° C. to the lithium isopropylamide solution. The mixture is stirred further at 0° C. until a clear orange-red solu-tion has resulted. At −65° C. 2.4 g (6.4 mmol) of 2Z-2-fluoro-3-[4,6-bis-(4-fluorophenyl)-2-(1-methylethyl)-pyrimidin-3-yl]-propene-2-aldehyde (Example 5a) in 20 ml of abs. THF are added dropwise, and the mixture is stirred further for 1 h. Subsequently 20 ml of 50% saturated ammonium chloride solution are added dropwise, the mixture is extracted with 2×50 ml of methylene chloride, and the org. extracts are washed 2× with water, dried with MgSO$_4$, filtered and concentrated.

Yield: 5.2 g of white crystals (87% of theory).
Melting point 193°-195° C.
$R_f$=0.29 (cyclohexane/ethyl acetate=4:1).
$^1$H NMR δ values in ppm: 1.30 (dd, 6H, CH$_3$), 1.55 (s, 2H, OH), 2.45 and 2.82 (d, 2H, CH$_2$), 3.2 (h, 1H, CH), 4.3-4.45 (m, 1H, CHOH), 5.95 (d, 1H J=38 Hz,

Z

CH=CF), 6.74, (s, 1H, CH—C$_6$H$_5$), 7.0-7.8 (m, 21H, aromat. prot.), 8.5-8.65 (m, 2H, aromat. prot.).
MS: m/e 714 C$_{44}$H$_{37}$N$_2$F$_3$O$_4$.

Example 6b–6l

The compounds VI b–VI l were prepared in a manner analogous to that described in Example 6a (cf. Tab. 5).

TABLE 5

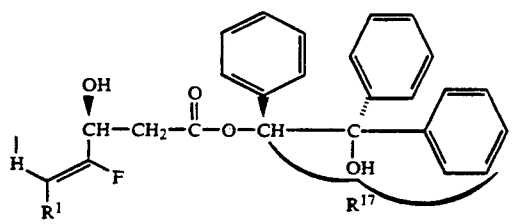

IV

| Example | Compound | R¹ | Yield % | $R_f$(Z) m.p. °C. (Z) | ¹H NMR δ/ppm = MS: m/e = |
|---|---|---|---|---|---|
| 6a | IVa | (4-fluorophenyl, isopropyl, methyl-substituted pyrimidine with 4-fluorophenyl) | 87% | cf. description Example 6a | |
| 6b | IVb | (4-fluorophenyl, isopropyl, methyl-substituted pyridine with phenyl) | 91% | $R_f$=0.31 | $C_{45}H_{39}F_2NO_4$ (695) |
| 6c | IVc | (isopropyl, methyl, bis(4-fluoro-3-methylphenyl) substituted alkene) | 78% | $R_f$=0.46 | $C_{44}H_{41}F_3O_4$ (690) |
| 6d | IVd | (4-fluorophenyl, isopropyl, methyl-substituted pyridazine with 4-fluorophenyl) | 65% | $R_f$=0.27 | $C_{44}H_{37}F_3N_2O_4$ (714) |

TABLE 5-continued

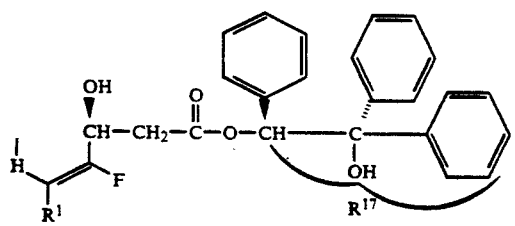

IV

| Example | Compound | R¹ | Yield % | R_f(Z)<br>m.p. °C. (Z) | ¹H NMR δ/ppm =<br>MS: m/e = |
|---|---|---|---|---|---|
| 6e | IVe | 4-(4-fluorophenyl)-3-methyl-2-isopropyl-1-phenylpyrrol-5-yl | 73% | R_f=0.36 | C₄₄H₃₉NF₂O₄ (683) |
| 6f | IVf | 4'-fluoro-5-(4-fluorophenyl)-3-isopropyl-2-methylbiphenyl-... | 92% | R_f=0.33 | C₄₆H₃₉F₃O₄ (712) |
| 6g | IVg | 6-(4-fluorophenyl)-5-methyl-4-isopropyl-2-isopropylpyrimidin-... | 69% | R_f=0.39 | C₄₁H₃₈N₂F₂O₄ (660) |
| 6h | IVh | 4-(4-fluorophenyl)-3-methyl-2-isopropyl-6-(4-fluorophenyl)pyridin-... | 77% | R_f=0.31 | C₄₅H₃₈F₃NO₄ (713) |

TABLE 5-continued

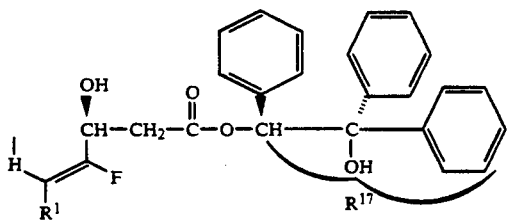

IV

| Example | Compound | R¹ | Yield % | $R_f$(Z) m.p. °C. (Z) | ¹H NMR δ/ppm = MS: m/e = |
|---|---|---|---|---|---|
| 6i | IVi | (3-methyl-2,4-bis(4-fluorophenyl)-pent-2-en-yl with isopropyl) | 92% | $R_f$=0.42 | $C_{42}H_{37}F_3O_4$ (662) |
| 6j | IVj | (4-(4-fluorophenyl)-5-methyl-3-tert-butyl-6-isopropyl-pyridazin-yl) | 59% | $R_f$=0.31 | $C_{42}H_{42}F_2N_2O_4$ (676) |
| 6k | IVk | (4-(4-fluorophenyl)-3-methyl-2-isopropyl-1-isopropyl-pyrrol-yl) | 81% | $R_f$=0.38 | $C_{41}H_{41}NF_2O_4$ (649) |
| 6l | IVl | (4'-fluoro-3,5-diisopropyl-2-methyl-biphenyl-yl) | 89% | $R_f$=0.40 | $C_{43}H_{42}F_2O_4$ (660) |

EXAMPLE 7

General Procedure For The Preparation Of Compounds Of The General Formula IV With $R^{17}=CH_3$

Example 7a

Methyl 4Z-3(S)-hydroxy-4-fluoro-5-[4,6-bis-(4-fluorophenyl)-2-(1-methylethyl)-pyrimidin-3-yl]-pent-4-ene-carboxylate 5.2 g (7.3 mmol) of 4Z-3-(S)-hydroxy-4-fluoro-5-[4,6-bis(4-fluorophenyl)-2-(1-methylethyl)-pyrimidin-3-yl]-pent-4-ene-carboxylic acid 2(S)-hytra ester (from Example 6a) in 50 ml of abs. methanol are added dropwise to a solution of 184 mg (8 mmol) of sodium in 50 ml of methanol. The mixture is stirred at room temperature for 16 h. After the reaction is complete, 0.5 ml of glacial acetic acid is added, then 30 ml of toluene are added and the mixture is concentrated in vacuo. The residue is dissolved in ether, and the ether phase is washed 2× with water, dried with MgSO₄, filtered and concentrated. Filtration through silica gel with cyclohexane/ethyl acetate=4:1 yields Yield: 3.25 g (97.6%) of pale oil.

$R_f$=0.25 (cyclohexane/ethyl acetate 4:1).

¹H NMR δ values in ppm: 1.38 (d, CH₃, 6H), 2.05 (s, 1H, OH), 2.4–2.7 (m, 2H, CH₂), 3.25 (h, 1H, CH), 3.75 (s, 3H, OCH₃), 4.5–4.6 (m, 1H, CHOH), 6.1 (d, 1H J=38 Hz, Z
CH=CF),
7.05-7.2 (m, 4H, aromat. prot.), 7.65-7.75 (m, 2H, aromat. prot.), 8.55-8.65 (m, 2H, aromat. prot.).

MS: m/e 456 $C_{25}H_{23}N_2F_3O_3$.

Example 7b–7l

The compounds IVm–IVx were prepared in a manner analogous to that described in Example 7a (cf. Tab. 6).

TABLE 6

IV

Structure: $R^1-CH=CF-CH(OH)-CH_2-C(O)-OCH_2-R^{17}$ (with the indicated OH, fluoroalkene geometry)

$R^{17} = CH_3$

| Example | Compound | R$^1$ | Yield % | R$_f$(Z) m.p. °C (Z) | $^1$H NMR δ/ppm = MS: m/e = |
|---|---|---|---|---|---|
| 7a | IVm | 2-(4-fluorophenyl)-5-isopropyl-4-methyl-6-(4-fluorophenyl)pyrimidin-... | 97.6% | | cf. description Example 7a |
| 7b | IVn | 2-phenyl-4-(4-fluorophenyl)-5-methyl-6-isopropyl-pyridin-... | 82% | R$_f$=0.27 | $C_{26}H_{25}F_2NO_3$ (437) |
| 7c | IVo | 1,2-bis(4-fluoro-3-methylphenyl)-3-methyl-4-methylpent-1-enyl | 71% | R$_f$=0.41 | $C_{25}H_{27}F_3O_3$ (432) |
| 7d | IVp | 3-isopropyl-4-methyl-5-(4-fluorophenyl)-6-(4-fluorophenyl)pyridazin-... | 87% | R$_f$=0.31 | $C_{25}H_{23}F_3N_2O_3$ (456) |

TABLE 6-continued $$\underset{R^1}{\overset{H}{\underset{}{\fbox{}}}}C=C\underset{F}{\overset{}{\underset{}{-}}}CH\underset{OH}{\overset{OH}{-}}CH_2-\overset{O}{\underset{}{C}}-OCH_2 \quad IV$$

$R^{17} = CH_3$

| Example | Compound | R¹ | Yield % | R_f (Z) m.p. °C. (Z) | ¹H NMR δ/ppm = MS: m/e = |
|---|---|---|---|---|---|
| 7e | IVq | [1-phenyl-2-isopropyl-3-methyl-4-(4-fluorophenyl)pyrrole] | 57% | R_f=0.32 | $C_{25}H_{25}NF_2O_3$ (425) |
| 7f | IVr | [3-isopropyl-2-methyl-1,1':3',1''-terphenyl with 4,4''-difluoro] | 68% | R_f=0.28 | $C_{27}H_{25}F_3O_3$ (454) |
| 7g | IVs | [2-isopropyl-5-isopropyl-4-methyl-6-(4-fluorophenyl)pyrimidine] | 69% | R_f=0.29 | $C_{22}H_{24}N_2FO_3$ (402) |
| 7h | IVt | [2-(4-fluorophenyl)-6-isopropyl-5-methyl-4-(4-fluorophenyl)pyridine] | 92% | R_f=0.27 | $C_{26}H_{23}F_3O_3$ (455) |

TABLE 6-continued

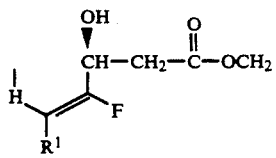

R^17 = CH3

| Example | Compound | R¹ | Yield % | R_f(Z) m.p. °C. (Z) | ¹H NMR δ/ppm = MS: m/e = |
|---|---|---|---|---|---|
| 7i | IVu | 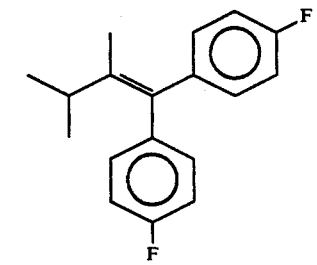 | 72% | R_f=0.38 | $C_{23}H_{23}F_3O_3$ (404) |
| 7j | IVv | 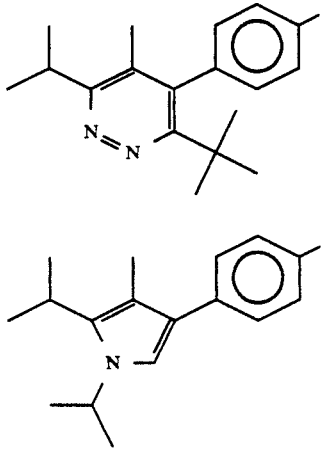 | 65% | R_f=0.37 | $C_{23}H_{28}F_2N_2O_3$ (418) |
| 7k | IVw | 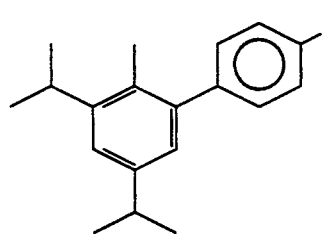 | 81% | R_f=0.39 | $C_{22}H_{27}NF_2O_3$ (391) |
| 7l | IVx | | 72% | R_f=0.30 | $C_{24}H_{28}F_2O_3$ (402) |

EXAMPLE 8

General Procedure For The Preparation Of Compounds Of The General Formula V

Example 8a

Tert.butyl 6Z-3-oxo-5(S)-hydroxy-6-fluoro-7-[4,6-bis-(4-fluorophenyl)-2-(1-methylethyl)-pyrimidin-3-yl]-hept-6-ene-carboxylate 12.5 ml (29 mmol) of butyllithium (15% strength solution in hexane) are added dropwise at −70° C. to 2.02 g (2.8 ml, 20 mmol) of diisopropylamine in 12.5 ml of abs. THF. The mixture is stirred at 0° C. for 30 min. It is then cooled to −70° C., and 2.33 g (20 mmol, 2.7 ml) of tert.-butyl acetate are added dropwise, and stirring at −70° C. is continued for 30 min, then 2.3 g (5 mmol) of methyl 4Z-3(S)-hydroxy-4-fluoro-5-[4,6-bis-(4-fluorophenyl)-2-(1-methylethyl)-pyrimidin-3-yl]-pent-4-ene-carboxylate (from Example 7a) in 25 ml of abs. THF are added dropwise at −70° C. The mixture is subsequently allowed to warm to R.T. and 60 ml of 50% saturated ammonium chloride solution are added. Extraction with 3×100 ml of methylene chloride is carried out. The CH2Cl2 extracts are washed with water, dried with MgSO4, filtered and concentrated in vacuo.

Yield: 3.1 g of pale oil (82% of theory).

R_f=0.54 (cyclohexane/ethyl acetate=2:1).

¹H NMR δ values in ppm: 1.38 (d, 6H, CH3), 1.45 (s, 9H, CH3), 1.6 (1H, s, OH), 2.5–2.9 (m, 2H, CH2), 3.2–3.4

(m, 2H, CH$_2$), 4.6–4.7 (m, 1H, CHOH), 6.1 (S, 1H, J=38 Hz, $$\overset{Z}{CH=CF)},$$

7.1–7.2 (m, 4H, aromat. prot.), 7.65–7.75 (m, 2H, aromat. prot.), 8.55–8.65 (m, 2H, aromat. prot.).
MS: m/e=540 C$_{30}$H$_{31}$N$_2$F$_3$O$_4$.

Example 8b–8l

The compounds Vb–Vl were prepared in a manner analogous to that described in Example 8a (cf. Tab. 7).

TABLE 7

V $$\underset{R^1}{\overset{H}{\underset{}{\diagdown}}}C=\underset{F}{\overset{}{C}}-\overset{OH}{\underset{}{CH}}-CH_2-\overset{O}{\underset{}{C}}-CH_2CO_2C_4H_9\text{-}t$$

| Example | Compound | R$^1$ | Yield % | R$_f$(Z) m.p. °C. (Z) | $^1$H NMR δ/ppm = MS: m/e = |
|---|---|---|---|---|---|
| 8a | Va | (4-F-C$_6$H$_4$)- and isopropyl-methyl-substituted pyrimidine with 4-F-phenyl | 82% | cf. description Example 8a | |
| 8b | Vb | isopropyl-methyl-(4-F-C$_6$H$_4$)-phenyl-pyridine | 69% | R$_f$=0.56 | C$_{31}$H$_{43}$F$_2$NO$_4$ (521) |
| 8c | Vc | bis(4-F-3-CH$_3$-C$_6$H$_3$)-isopropyl-methyl alkene | 81% | R$_f$=0.70 | C$_{30}$H$_{35}$F$_3$O$_4$ (516) |
| 8d | Vd | isopropyl-methyl-bis(4-F-C$_6$H$_4$)-pyridazine | 72% | R$_f$=0.61 | C$_{30}$H$_{31}$F$_3$N$_2$O$_4$ (540) |

TABLE 7-continued
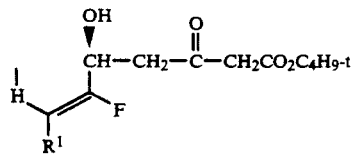
| Example | Compound | R¹ | Yield % | $R_f$(Z) m.p. °C. (Z) | ¹H NMR δ/ppm = MS: m/e = |
|---|---|---|---|---|---|
| 8e | Ve | | 59% | $R_f$=0.59 | $C_{30}H_{33}NF_2O_2$ (509) |
| 8f | Vf | | 77% | $R_f$=0.56 | $C_{32}H_{33}F_3O_4$ (538) |
| 8g | Vg | | 66% | $R_f$=0.62 | $C_{27}H_{32}N_2F_2O_4$ (486) |
| 8h | Vh | | 77% | $R_f$=0.57 | $C_{31}H_{32}F_3NO_4$ (539) |
| 8i | Vi | | 86% | $R_f$=0.68 | $C_{28}H_{31}F_3O_4$ (488) |

TABLE 7-continued $$\underset{H}{\overset{R^1}{\underset{|}{C}}}=\overset{F}{\underset{|}{C}}-\overset{OH}{\underset{|}{CH}}-CH_2-\overset{O}{\underset{\|}{C}}-CH_2CO_2C_4H_9\text{-}t \qquad V$$

| Example | Compound | R¹ | Yield % | R$_f$(Z) m.p. °C. (Z) | ¹H NMR δ/ppm = MS: m/e = |
|---|---|---|---|---|---|
| 8j | Vj | 4-(4-fluorophenyl)-6-isopropyl-5-methyl-3-tert-butyl-pyridazin-yl | 69% | R$_f$=0.65 | C$_{28}$H$_{36}$F$_2$N$_2$O$_4$ (502) |
| 8k | Vk | 4-(4-fluorophenyl)-2-isopropyl-3-methyl-1-isopropyl-pyrrol-yl | 62% | R$_f$=0.58 | C$_{27}$H$_{35}$NF$_2$O$_4$ (475) |
| 8l | Vl | 4'-fluoro-3,5-diisopropyl-2-methyl-biphenyl-yl | 76% | R$_f$=0.52 | C$_{29}$H$_{36}$F$_2$O$_4$ (486) |

EXAMPLE 9

General Procedure For The Preparation Of Compounds Of The General Formula I (R²=t—C₄H₉)

Example 9a tert. Butyl 6Z-3(R),5(S)-dihydroxy-6-fluoro-7-4,6-bis-(4-fluorophenyl)-2-(1-methylethyl)-pyrimidin-3-yl]-hept-6-enecarboxylate 10 ml of methanol in 40 ml of abs. THF are added dropwise to a solution of 5.5 ml (5.5 mmol) of triethylborane (1 mole/liter) in abs. THF, and the mixture is stirred at R.T. for 1 h. At −70° C. 2.5 g (5 mmol) of tert. butyl 6Z-3-oxo-5(S)-hydroxy-6-fluoro-7-[4,6-bis-(4-fluorophenyl)-2-(1-methylethyl)-pyrimidin-3-yl]-hept-6-enecarboxylate (from Example 8a) in 20 ml of abs. THF are added dropwise, and the mixture is stirred for 30 min. Then 210 mg (5.5 mmol) of sodium borohydride are added and the mixture is stirred at −70° C. After the reaction is complete, 0.5 ml of glacial acetic acid in 3 ml of toluene is added in the cold, and stirring is continued for 5 min. Subsequently 50 ml of 50% saturated sodium bicarbonate solution are added at R.T., and the mixture is extracted with methylene chloride. The org. extracts are dried with MgSO₄, filtered, concentrated in vacuo and filtered through silica gel (cyclohexane/ethyl acetate=2:1)

Yield: 3.0 g of pale crystals (92.3% of theory), melting point 148° C.

R$_f$=0.325 (cyclohexane/ethyl acetate=2:1).

¹H NMR δ values in ppm: 1.35 (d, 6H, CH₃), 1.5 (s, 9H, CH₃), 1.42–1.6 (m, 2H, CH₂), 2.4 (d, 2H, CH₂CO₂-tert.but), 3.3 (h, 1H, CH), 3.9 (s, 1H, OH), 4.1 (s, 1H, OH), 4.12–4.28 (m, 1H, CHOH), 4.35–4.45 (m, 1H, CHOH), 6.08 (d, 1H, J=38 Hz, CH=CF), 7.05–7.15 (m, 1H, aromat. prot.), 7.7–7.8 (m, 1H, aromat. prot.), 8.55–8.65 (m, 2H, aromat. prot.).

MS: m/e=540 C₃₀H₃₁N₂F₃O₄.

Example 9b–9l

The compounds I b–I l are prepared in a manner analogous to that described in Example 9a (cf. Tab. 8).

TABLE 8

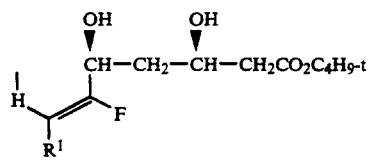
I

| Example | Compound | R¹ | Yield % | $R_f$(Z) m.p. °C. (Z) | ¹H NMR δ/ppm = MS: m/e = |
|---|---|---|---|---|---|
| 9a | Ia | (4-fluorophenyl, methyl, isopropyl-substituted pyrimidine with 4-fluorophenyl) | 92.3% | cf. description Example 9a | |
| 9b | Ib | (4-fluorophenyl, methyl, isopropyl-substituted pyridine with phenyl) | 78% | $R_f$=0.33 | $C_{31}H_{45}F_2NO_4$ (523) |
| 9c | Ic | (bis(4-fluoro-3-methylphenyl), methyl, isopropyl alkene) | 69% | $R_f$=0.39 | $C_{30}H_{37}F_3O_4$ (518) |
| 9d | Id | (4-fluorophenyl, methyl, isopropyl-substituted pyridazine with 4-fluorophenyl) | 73% | $R_f$=0.37 | $C_{30}H_{33}F_3N_2O_4$ (542) |
| 9e | Ie | (4-fluorophenyl, methyl, isopropyl-substituted N-phenylpyrrole) | 82% | $R_f$=0.42 | $C_{30}H_{35}F_2NO_4$ (511) |

TABLE 8-continued
$$\underset{R^1}{\overset{H}{>}}C=\underset{F}{\overset{OH}{\underset{|}{C}}}-CH\overset{OH}{\underset{|}{-}}CH_2-CH-CH_2CO_2C_4H_9\text{-}t \qquad I$$
| Example | Compound | R¹ | Yield % | $R_f(Z)$<br>m.p. °C. (Z) | ¹H NMR δ/ppm =<br>MS: m/e = |
|---------|----------|-----|---------|--------------------------|------------------------------|
| 9f | If | 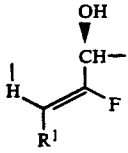 | 69% | $R_f=0.28$ | $C_{32}H_{35}F_3O_4$ (540) |
| 9g | Ig | 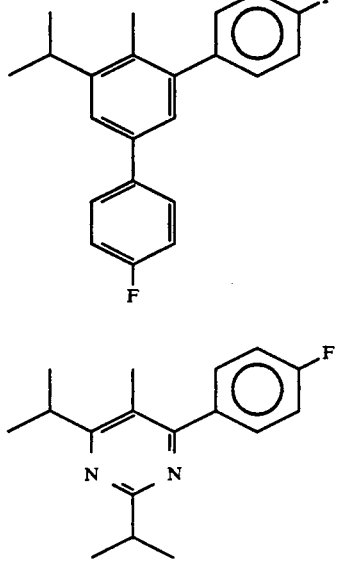 | 88% | $R_f=0.36$ | $C_{27}H_{34}N_2F_2O_4$ (488) |
| 9h | Ih | 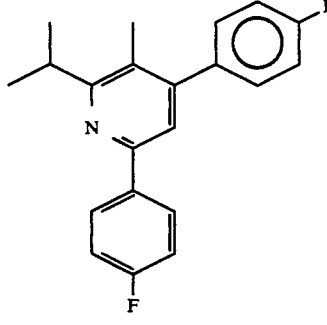 | 86% | $R_f=0.32$ | $C_{31}H_{34}F_3NO_4$ (541) |
| 9i | Ii | 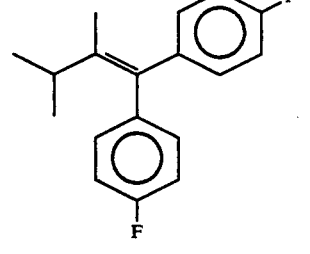 | 78% | $R_f=0.41$ | $C_{28}H_{33}F_3O_4$ (490) |
| 9j | Ij | 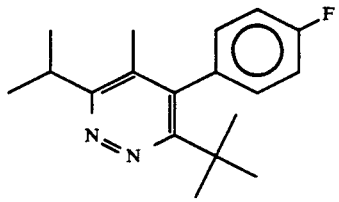 | 82% | $R_f=0.39$ | $C_{28}H_{38}F_2N_2O_4$ (504) |

TABLE 8-continued

Structure: CH(H)(R¹)=CF—CH(OH)—CH₂—CH(OH)—CH₂CO₂C₄H₉-t  (I)

| Example | Compound | R¹ | Yield % | R_f (Z) m.p. °C. (Z) | ¹H NMR δ/ppm = MS: m/e = |
|---|---|---|---|---|---|
| 9k | Ik | 1-isopropyl-2-isopropyl-3-methyl-4-(4-fluorophenyl)pyrrol-4-yl | 69% | R_f=0.44 | C₂₇H₃₇NF₂O₄ (477) |
| 9l | Il | 2-methyl-3,5-diisopropyl-4'-fluorobiphenyl-yl | 59% | R_f=0.30 | C₂₉H₃₈F₂O₄ (488) |

EXAMPLE 10

General Procedure For The Preparation Of Compounds Of The General Formula II

Example 10a

Z-6(S)-2-[(4,6-bis-(4-fluorophenyl)-2-(1-methylethyl)-pyrimidin-3-yl)]-(1-fluoro-2-ethenyl)-4(R)-hydroxy-3,4,5,6-tetrahydro-2H-pyran-2-one 2.7 g (5 mmol) of tert. butyl 6Z-3(R), 5(S)-dihydroxy-6-fluoro-7-[4,6-bis-(4-fluorophenyl)-2-(1-methylethyl)-pyrimidin-3-yl]-hept-6-enecarboxylate (Example 9a) are dissolved in 50 ml of methylene chloride, and 3.99 g (2.7 ml, 35 mmol) of trifluoroacetic acid are added. The mixture is stirred at R.T. for 6 h and then neutralized with potassium bicarbonate solution and extracted 2× with diethyl ether. The ether extracts are dried with MgSO₄, filtered, concentrated and filtered through silica gel.

Yield: 1.39 g (70% of theory) white crystals of melting point 198° C.
Optical rotation: $[\alpha]_D^{25} = -13.2°$ (CH₃OH, C=1).
R_f=0.13 (cyclohexane/ethyl acetate=2:1).
¹H NMR δ values in ppm: 1.38 (d, 6H, CH₃), 1.55 (s, 1H, OH), 1.8–2.0 (m, 2H, CH₂), 2.6–2.8 (m, 2H, CH₂CO), 3.25 (h, 1H, CH), 4.35–4.45 (m, 1H, CHOH), 5.15–5.35 (m, 1H, CHOCO), 6.1 (d, 1H, J=35 Hz,

Z
CH=CF), 7.1–7.2 (m, 4H, aromat. prot.), 7.6–7.75 (m, 2H, aromat. prot.), 8.5–8.6 (m, 2H, aromat. prot.).
MS: m/e=468 C₂₆H₂₃N₂F₃O₃.

Example 10 b–10l

The compounds II b–II l were prepared in a manner analogous to that described in Example 10a (cf. Tab. 9).

TABLE 9

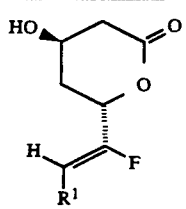

| Example | Compound | R¹ | Yield % | R$_f$(Z) m.p. °C. (Z) | ¹H NMR δ/ppm = MS: m/e = |
|---|---|---|---|---|---|
| 10a | IIa | *(4-fluorophenyl/isopropyl/methyl substituted pyrimidine with 4-fluorophenyl)* | 70% | | cf. description Example 10a |
| 10b | IIb | *(isopropyl/methyl pyridine with 4-fluorophenyl and phenyl substituents)* | 72% | R$_f$=0.15 Fp. 165–167° C. | $C_{27}H_{25}F_2NO_3$ (499) NMR: 1.35(d, 6H), 1.5–1.95(m, 2H), 2.55–2.80(m, 2H), 3.35(h, 1H), 4.35–4.45(m, 1H), 5.15–5.25(m, 1H) 6.10(d, 1H, J=36Hz) 7.1–7.2(m, 2H), 8.5–8.6(m, 2H), 7.45–7.55(m, 3H) Fp. 165–167° C. 7.65–7.75(m, 2H) |
| 10c | IIc | *(isopropyl alkene with two 4-fluoro-3-methylphenyl groups)* | 81% | R$_f$=0.22 | $C_{26}H_{27}F_3O_3$ (444) NMR: 1.08(d, 6H), 1.85–1.75 und 1.60–1.52 (each m, total 3H) 2.25 und 2.20 (each s, each 3H), 2.56(dd, J=18Hz, J$_2$=4Hz, 1H), 2.7(dd, J$_1$=18Hz, J$_2$=4Hz, 1H) 2.87(h, 1H), 4.22(m, 1H), 5.05(m, 1H) 6.4–7.1(m, 7H) |
| 10d | IId | *(isopropyl/methyl pyridazine with two 4-fluorophenyl groups)* | 68% | R$_f$=0.20 | $C_{26}H_{23}F_3N_2O_3$ (468) NMR: 1.44(dd, J=7Hz, 6H), 1.52–1.93(m, 3H); 2.61–2.84(m, 2H), 3.45(h, 1H), 5.2(m, 1H) 6.12(d, 1H, J=37Hz), 7.00–7.41(m, 8H) |
| 10e | IIe | *(isopropyl/methyl N-phenylpyrrole with 4-fluorophenyl)* | 72% | R$_f$=0.16 | $C_{26}H_{25}NF_2O_3$ (437) NMR: 1.3(dd, 6H), 1.5–1.7(m, 2H), 2.0–2.3(m, 2H), 2.6–2.9 (broad s, 1H), 3.1(h, 1H), 4.2–4.25(m, 1 5.1–5.2 (m, 1H), 6.12(d, 1H, J=36Hz), 6.5(s, 1H) 6.9–7.5(m, 9H) |

TABLE 9-continued

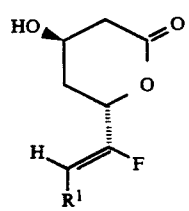

| Example | Compound | R[1] | Yield % | R$_f$(Z) m.p. °C. (Z) | $^1$H NMR δ/ppm = MS: m/e = |
|---|---|---|---|---|---|
| 10f | IIf | (2-methyl-3-isopropyl-5-(4'-fluorophenyl)phenyl with 4-fluorophenyl) | 86% | R$_f$=0.15 | C$_{28}$H$_{25}$F$_3$O$_3$ (466)<br>NMR:<br>1.3(dd, 6H), 1.6(s, 1H), 1.7-2.0(m, 2H)<br>2.55-2.80(m, 2H), 3.45(h, 1H), 5.23(m, 1H), 4.2-4 (m, 1H), 6.10(d, 1H, J=36Hz), 7.1-7.6(m, 10H) |
| 10g | IIg | (pyrimidine with isopropyl, methyl, 4-fluorophenyl, isopropyl) | 72% | R$_f$=0.22<br>m.p. 138° C. | C$_{23}$H$_{24}$N$_2$F$_2$O$_3$ (414)<br>NMR:<br>1.25(d, 6H), 1.38(d, 6H), 1.75-2.0(m, 2H), 1.5-1.7 (broad s, 1H), 2.6-2.8(m, 2H), 3.1-3.3(m, 2H), 4.32-4.40(m, 1H), 5.15-5.3(m, 1H), 6.02 (d, J=36Hz, 1H), 7.05-7.15(m, 2H), 7.5-7.65(m, 2H) |
| 10h | IIh | (pyridine with isopropyl, methyl, 4-fluorophenyl, 4-fluorophenyl) | 78% | R$_f$=0.16 | C$_{27}$H$_{24}$NF$_3$O$_3$ (467)<br>NMR:<br>(analogous to Ex. 10b, 7.1-8.2(m, 8H)) |
| 10i | IIi | (alkene with methyl, isopropyl, two 4-fluorophenyls) | 63% | R$_f$=0.25 | C$_{24}$H$_{23}$F$_3$O$_3$ (416)<br>NMR:<br>1.1(d, 6H), 1.55-1.68 und 1.73-1.90 (each m, total 3H) 2.57(dd, J$_1$=17Hz, J$_2$=4Hz, 1H), 2.70(dd, J$_1$=17Hz, J$_2$=4Hz, 1H), 2.87(h, 1H), 4.25(m, 1H), 5.05(m, 1H), 6.4-7.1(m, 9H) |

TABLE 9-continued

[Structure II: HO-substituted tetrahydropyran-2-one with vinyl fluoride substituent bearing R¹]

| Example | Compound | R¹ | Yield % | $R_f$(Z) m.p. °C. (Z) | ¹H NMR δ/ppm = MS: m/e = |
|---|---|---|---|---|---|
| 10j | IIj | [4-(4-fluorophenyl)-3-methyl-6-isopropyl-2-tert-butyl-pyridazin-5-yl] | 72% | $R_f$=0.20 | $C_{24}H_{28}F_2N_2O_3$ (430) NMR: (analogous Ex. 10d, 7.00–7.41(m, 4H) 1.1(s, 9H |
| 10k | IIk | [4-(4-fluorophenyl)-3-methyl-2-isopropyl-1-isopropyl-pyrrol-5-yl] | 81% | $R_f$=0.24 | $C_{23}H_{27}NF_2O_3$ (403) NMR: 1.35 und 1.45 (each 6H, d), 1.5–1.8(m, 2H) 2.55–2.75(m, 2H), 2.6 (broad s, 1H), 3.3(h, 1H) 4.25–4.35(m, 1H), 5.2–5.3(m, 1H), 4.4(h, 1H) 6.05(d, 1H, J=36Hz), 6.5–7.35 (aromat. protons) |
| 10l | IIl | [4'-fluoro-3,5-diisopropyl-2-methyl-biphenyl-yl] | 68% | $R_f$=0.26 | $C_{25}H_{28}F_2O_3$ (414) NMR: 1.3(dd, 6H), 1.65(s, 1H), 1.7–2.0(m, 2H) 2.55–2.75(m, 2H), 2.9 and 3.4 (each 1H, h) 4.3–4.4(m, 1H), 5.20–5.28(m, 1H), 6.08(d, 1H, J=36Hz) 6.95–7.55(m, 6H) |

Example 10m

The compound of the formula II in which R¹ represents a pyrimidine radical of the formula

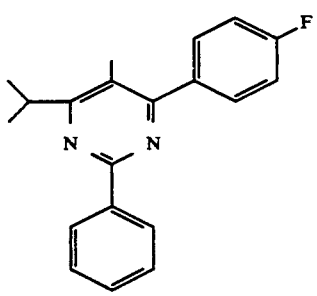

is obtained in a manner analogous to that described in the previous examples. It has a melting point of 195°–197° C.

EXAMPLE 11

General Procedure For The Preparation Of Compounds Of The General Formula I R²=H

Example 11a 6Z-3(R), 5(S)-Dihydroxy-6-fluoro-7-[4,6-bis-(4-fluorophenyl)-2-(1-methylethyl)-pyrimidin-3-yl]-hept-6-ene-carboxylic acid 1 eq. of 10% strength aqueous sodium hydroxide solution is added to a solution of 0.5 g of tert. butyl 6Z-3(R), 5(S)-dihydroxy-6-fluoro-7-[4,6-bis-(4-fluorophenyl)-2-(1-methylethyl)-pyrimidin-3-yl]-hept-6-ene-carboxylate (Example 9a) in 5 ml of ethanol, and the mixture is stirred at room temperature for 3 h. The pH is then adjusted to 3–4 with 0.5 N hydrochloric acid in the cold, saturated brine is added, and the mixture is extracted 3× with ethyl acetate. The org. extracts are dried with MgSO₄, filtered and concentrated in vacuo.

Yield: 0.42 g (92% of theory) of pale oil.

$R_f$0.13 (cyclohexane/ethyl acetate=2:1).

¹H NMR δ values in ppm: (in DMSO) 1.3 (d, 6H, CH₃), 1.5–1.65 (m, 2H, CH₂), 1.75 (s, 1H, OH), 2.0–2.3 (m, 2H, CH₂), 3.3 (h, 1H, CH), 3.7–3.9 (m, 1H, CHOH), 4.15–4.3 (m, 1H, CHOH), 6.15 (d, 1H J=36 Hz,

Z
CH=CF), 7.25–7.4 (m, 4H, aromat. prot.), 7.8–7.9 (m, 2H, aromat. prot.), 8.45–8.55 (m, 2H, aromat. prot.), 5.5–5.9 (broad s, 1H, COOH).

MS: m/e=540.

Example 11 b–11 l

The compounds of the formula I with $R^2$=H corresponding to Example 11 b–11 l are prepared in a manner analogous to that described in Example 11a.

It is also possible under the same reaction conditions as in Example 11a to hydrolyze the lactones of the general formula II (Example 10a) to the free carboxylic acids or the salts thereof.

We claim:

1. (3R,5S,6E)-6-Fluoro-3,5-dihydroxy-hept-6-enoic acids and the derivatives thereof of formula I

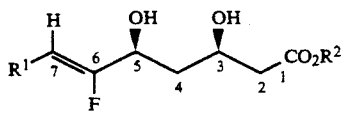

and the corresponding (4R,6S)-6-(1-fluoro-vinyl)-4-hydroxytetrahydro-pyran-2-ones of formula II

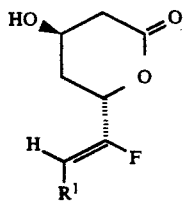

where, in formulas I and II, $R^1$ denotes the group of substituted 6-membered ring heteroaromatics

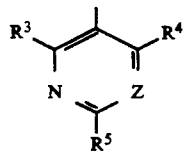

in which

Z denotes a nitrogen atom, and $R^3$, $R^4$ and $R^5$ independently denote hydrogen, a straight chain or branched alkyl or alkenyl radical, each of which has up to 6 carbon atoms and which can optionally be substituted on the terminal carbon by a cycloalkyl or cycloalkenyl radical, each of which has 3–6 carbon atoms, or denote a cyclic hydrocarbon radical which is saturated or up to doubly saturated and has 3–7 carbon atoms, or an aromatic radical selected from the group consisting of phenyl, furyl, thienyl and pyridinyl, which can optionally carry in the nucleus 1–3 identical or different substituents from the following group: halogen, trifluoromethyl, alkyl or alkenyl, each of which has up to 6 carbon atoms, hydroxyl, alkoxy having 1–6 carbon atoms, carboxyl or carbalkoxy having 1–6 carbon atoms in the alkoxy moiety.

2. A pharmaceutical composition for the prophylaxis or therapy of arteriosclerosis or hypercholesterolemia comprising an effective amount of a compound as claimed in claim 1 and a pharmaceutically acceptable carrier.

3. A method for the prophylaxis and therapy of arteriosclerosis and hypercholesterolemia comprising administering to a host a pharmaceutically effective amount of a compound as claimed in claim 1.

* * * * *